United States Patent [19]

Sawaki et al.

[11] Patent Number: 4,795,754

[45] Date of Patent: Jan. 3, 1989

[54] 3-(1H-TETRAZOL-5-Y1)OXANILIC ACID AND SALTS THEREOF AND PHARMACEUTICAL COMPOSITIONS CONTAINING THEM

[75] Inventors: Shohei Sawaki, Kanagawa; Yasuhiro Ootake, Sagamihara; Terumasa Hashimoto, Hatano; Tooru Abe, Sagamihara; Yoshihiro Horio, Matano, all of Japan

[73] Assignee: Wakamoto Pharmaceutical Co., Ltd., Tokyo, Japan

[21] Appl. No.: 82,640

[22] Filed: Aug. 7, 1987

[30] Foreign Application Priority Data

Aug. 12, 1986 [JP] Japan ................... 61-187683

[51] Int. Cl.$^4$ .................... C07D 257/04; A61K 31/41
[52] U.S. Cl. ..................................... 514/381; 548/253
[58] Field of Search ......................... 548/253; 514/381

[56] References Cited

U.S. PATENT DOCUMENTS

| | | | |
|---|---|---|---|
| 4,400,381 | 8/1983 | Favier et al. | 544/381 X |
| 4,432,986 | 2/1984 | Erickson | 548/253 X |
| 4,442,115 | 4/1984 | Ramsden et al. | 548/253 X |
| 4,443,460 | 4/1984 | Rodrigez et al. | 564/239 X |

FOREIGN PATENT DOCUMENTS

| | | |
|---|---|---|
| 56-40673 | 4/1981 | Japan. |
| 57-11975 | 1/1982 | Japan. |

OTHER PUBLICATIONS

"Procedures for immunochemical study of histamine release from leukocytes with small volume of blood", Charles D. May, M. D., et al., *J. Allerg.*, vol. 46, No. 1, pp. 12-20 (Jul., 1970).
"Antiallergic Properties of an Orally Effective Agent, [[3-(1H-Tetrazol-5-yl)Phenyl]Amino] Oxoacetic Acid n-Butyl Ester", Mitsuji Agata, et al., *Japan. J. Pharmacol.*, 32, 689-697 (1982).

*Primary Examiner*—Glennon H. Hollrah
*Assistant Examiner*—D. B. Springer
*Attorney, Agent, or Firm*—Burns, Doane, Swecker & Mathis

[57] ABSTRACT

A new compound, 3-(1H-tetrazol-5-yl)oxanilic acid and pharmaceutically acceptable salts thereof are herein disclosed, which can be prepared by reacting 3-(1H-tetrazol-5-yl)aniline with a compound represented by the general formula: A—CO—CO—B (wherein A and B may be identical with or different from one another and represent hydroxyl group, a halogen atom or a lower alkoxy group) and then optionally hydrolyzing the resultant product. The compound presents an excellent histamine and SRS-A release inhibitory effect and is hydrophilic or soluble in water. Therefore, the compound is very suitable to form, in particular, an aqueous pharmaceuticals for treatment or prevention of allergic diseases such as bronchial asthma, rhinitis and conjunctivitis.

6 Claims, No Drawings

3-(1H-TETRAZOL-5-YL)OXANILIC ACID AND SALTS THEREOF AND PHARMACEUTICAL COMPOSITIONS CONTAINING THEM

BACKGROUND OF THE INVENTION

1. Field of the Invention

The present invention relates to 3-(1H-tetrazol-5-yl)-oxanilic acid and salts thereof which are hydrophilic or soluble in water, a method for preparing these compounds and the use of them as antiallergic agent for treating and preventing allergic diseases such as bronchial asthma, rhinitis and conjunctivitis.

2. Description of the Prior Art

It has been known that there are a lot of morbigenous antigens in the living environment, which possibly cause allergic reaction in human body, such as house dusts, pollen, molds, drugs (e.g., aspirin, penicillin) or the like. Among allergic reactions, bronchial asthma or the like are referred to as IgE dependent type allergy in which IgE is strongly involved. If an antigen comes into contact with the surface of the cell membrane of a mast cell, the antigen and IgE antibody cause an antigen-antibody reaction. As a result, degranulation phenomenon is caused and the resulting granule secretes various chemical transmitters such as histamine, SRS-A (slow reacting substance of anaphylaxis), ECF-A (eosinophil chemotactic factor of anaphylaxis), heparin or the like thereby various kinds of allergic reaction are caused. In other words, the allergic diseases are caused as a result of hypersecretion of mucous gland, contraction of smooth muscles or the like because of the foregoing antigen-antibody reaction.

Among the foregoing chemical transmitters, histamine, SRS-A and ECF-A are considered to be particularly important so far as the human body is concerned. Therefore, it is effective to suppress the secretion of these chemical transmitters to protect and treat patients suffering from such diseases.

Thus, there have been proposed a variety of pharmaceutical preparations containing active components having histamine and SRS-A release inhibitory effect. Among them, drugs effective to asthma or other allergic diseases such as esters of 3-(1H-tetrazol-5-yl)oxanilic acid, for instance, ethyl ester and butyl ester thereof (hereunder referred to as MTB) have been known. In this respect, reference is made to Japanese Patent Publication for Opposition Purpose No.59-1705 (antiallergic compound) and Japanese Patent Unexamined Publication Nos. 61-151116 and 61-225121 (agent for treating asthma).

These esters of 3-(1H-tetrazol-5-yl)oxanilic acid such as MTB presents an excellent histamine and SRS-A release inhibitory effect and, therefore, they may be used as antiallergic agents and/or drugs for treatment or prevention of asthma. However, it is quite difficult to prepare an aqueous pharmaceutical preparation of these esters for some purposes and in general they are used in the dosage form of orally administered solid preparations since these compounds are hydrophobic or less soluble in water (Japanese Journal of Pharmacology, 1982, Vol. 32, pp. 689-697).

Generally speaking, when these compounds are used as drugs for treatment or prevention of asthma, it is preferred to adminster, to patients, such a drug locally and in the minimum effective amount thereof for the purpose of preventing the occurrence of any possible side effects which are possibly caused due to systemic administration of a large amount of drugs.

Accordingly, it is very desirable to adminster these drugs as an inhalant which makes it possible to administer the drugs even to the deep portion of the bronchus in the form of the fine particles of the solution thereof. For this reason, the drugs for treatment or prevention of asthma should be hydrophilic or soluble in water.

SUMMARY OF THE INVENTION

As explained above, in order to effectively treat or protect from allergic diseases such as bronchial asthma, rhinitis and conjunctivitis without causing any side effects, it is required to administer drugs therefor to patients in the form of local type formulations, e.g., an inhalant, eye drop, nasal drop, etc. and for this reason the drugs are desirable to be hydrophilic or soluble in water. Under such circumstances, the inventors of the present invention have conducted studies to obtain compounds which are hydrophilic or soluble in water and have a high efficiency for treating or preventing allergic diseases.

Accordingly, it is a principal purpose of the present invention to provide compounds effective for treating or preventing asthma, which are hydrophilic or soluble in water.

It is another purpose of the present invention to provide a method for preparing compounds useful as a drug for treating or preventing allergic diseases.

It is a further purpose of the present invention to provide pharmaceutical preparations for treating or protecting human bodies from allergic diseases such as bronchial asthma, rhinitis and conjunctivitis, for instance, inhalant, resolution for eye drop and nasal drop in the form of aqueous solutions.

The aforementioned and other purposes according to the present invention can effectively be achieved by providing 3-(1H-tetrazol-5-yl)oxanilic acid represented by the following formula [I]:

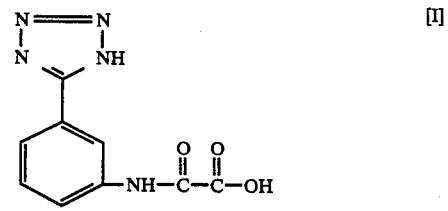

and pharmaceutically acceptable salts thereof. The compound according to the present invention can be prepared by reacting 3-(1H-tetrazol-5-yl)aniline represented by the following formula [II]:

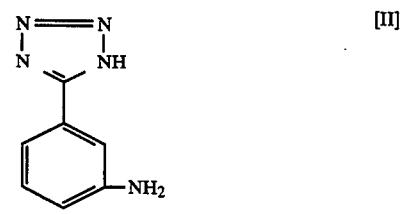

with oxalic acid or a reactive derivative thereof represented by the following general formula [III]:

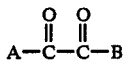

wherein A and B may be identical with or different from each other and represent a halogen atom, a lower alkoxy group or hydroxyl group, to form 3-(1H-tetrazol-5-yl)oxanilic acid or a derivative thereof represented by the following general formula [IV]:

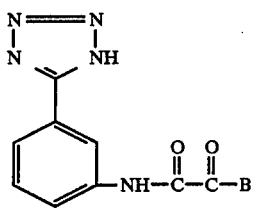

wherein B represents the same meanings as that defined above, and then optionally hydrolyzing the resultant compound (IV).

Preferred pharmaceutically acceptable salts of the compound of the present invention include, for instance, alkali metal salts such as sodium and disodium salt and potassium salt.

The foregoing compound represented by the formula [I] according to the present invention is a new compound which has not been reported in the literature at all and is hydrophyilic or soluble in water and presents an excellent histamine and SRS-A release inhibitory effect, therefore, this compound can effectively be used as antiallergic agents such as those for treating or preventing rhinitis, conjunctivitis and bronchial asthma without causing a severe side effect since it can be administered locally to patients in the form of inhalant, eye drop, nasal drop or the like.

The method for preparing the compounds according to the present invention will hereunder be described in more detail. First of all, the reaction of the compound represented by the general formula [II] with that represented by the general formula [III] may in general be carried out in an inert solvent such as chloroform, methylene chloride, benzene, toluene, acetone, tetrahydrofuran, dimethylformamide and dimethoxyethane.

The reaction conditions may vary widely depending on the kind of the starting material represented by the general formula [III]. For example, when an acid per se is used as the starting material, it is preferred to carry out the reaction in the presence of an agent for dehydration-condensation such as DCC, when a lower alkyl ester is used as the staring material, the reaction can be carried out at a temperature of from 100° to 180° C. without using any solvent since the starting material also serves as a solvent and when an acid halide is used as the starting material, the reaction can be completed at room temperature within a relatively short period of time.

When the products obtained at this stage represented by the general formula [IV] are acid, the products may be used as it is by simply separating it, while if the products are halides or esters, they must be hydrolyzed to convert them to a desired acid form and then separated for final usage.

The hydrolysis of the halides may be effected by simply bringing them into contact with water and on the other hand, the esters may also easily be hydrolyzed according to any alkali hydrolysis techniques which are well-known in the art.

The salts of the compounds according to the present invention may also be prepared according to any known method for converting the carboxylic acids to their salts.

The present invention will now be explained in more detail with reference to the following examples, however, it is not intended to restrict the scope of this invention to these specific examples which are given only for illustrating the present invention.

EXAMPLE 1

Preparation of (3-1H-Tetrazol-5-yl)Oxanilic Acid

Five grams of 3-(1H-tetrazol-5-yl)aniline was dissolved in 25 ml of N,N'-dimethylformamide, followed by adding 5.68 g of triethylamine. Then, 5.64 g of ether oxalyl chloride was dropwise added to the solution while cooling in ice water. After completion of the dropwise addition, the reaction temperature was slowly raised up to room temperature and the reaction was continued for 15 hours. After the reaction was completed, the reaction mixture was poured into 100 ml of ice water and crystals separated out from the solution was filtered off to obtain 8.3 g of ethyl 3-(1H-tetrazol-5-yl)oxanilate (yield 94.1%). This was recrystallized from acetone/n-hexane and the purified compound having a m.p. of 192°–193° C. was recovered.

Elemental Analysis (for $C_{11}H_{11}N_5O_3$)

|  | C (%) | H (%) | N (%) |
|---|---|---|---|
| Calcd. | 50.57 | 4.24 | 26.81 |
| Found | 50.62 | 4.19 | 26.98 |

N.M.R. Spectra (DMSO-$d_6$; 60MHz)

| δ (ppm): 1.38 (t, 3H), 4.42 (q, 2H), 7.43–8.20 (m, 3H), 8.73–8.80 (m, 1H), 9.81 (br.s, 1H), 11.21 (br.s, 1H) |
|---|

I.R. Spectra (nujol): 1690 cm$^{-1}$ (carbonyl group).

The product, ethyl 3-(1H-tetrazol-5-yl)oxanilate (5 g), was dissolved in 35 ml of ethanol and 100 ml of 0.5N sodium hydroxide was dropwise added thereto under water cooling. After the dropwise addition, the reaction temperature was slowly raised up to room temperature and under such condition, the reaction was carried out for 3 hours. This solution was dropwise added to 70 ml of 4N hydrochloric acid at room temperature. Thereafter, the solution was stirred for one hour and crystals separated out from the solution was filtered off. The resultant crystals were washed with water and 3.9 g of 3-(1H-tetrazol-5-yl)oxanilic acid was recovered (yield 87.4%). The product was recrystallized from isopropyl alcohol/water. m.p. 241°–243° C. (decomposed).

Elemental Analysis (for $C_9H_7N_5O_3$)

|  | C (%) | H (%) | N (%) |
|---|---|---|---|
| Calcd. | 46.35 | 3.03 | 30.04 |
| Found | 46.50 | 2.95 | 30.16 |

N.M.R. Spectra (DMSO-$d_6$; 60MHz)

| δ (ppm): 7.51–8.27 (m, 3H), 8.65–8.93 (m, 1H), |
|---|

-continued 11.17 (br.s, 1H)

I.R. Spectra (KBr disc): 1670 cm$^{-1}$ (carbonyl group).

On the other hand, when the drying procedure was gently carried out, the monohydrate of the title compound was obtained.

m.p. 240° C. (decomposed; the crystal water was removed at 100° C.).

Elemental Analysis (for $C_9H_7N_5O_3$—$H_2O$)

|  | C (%) | H (%) | N (%) |
| --- | --- | --- | --- |
| Calcd. | 43.03 | 3.61 | 27.88 |
| Found | 43.16 | 3.59 | 27.79 |

N.M.R. Spectra (DMSO-$d_6$; 60MHz)

δ (ppm): 7.53–8.33 (m, 3H), 8.65–8.93 (m, 1H), 8.83–9.21 (br.s, 2H), 11.16 (br.s, 1H)

I.R. Spectra (KBr disc): 1680 cm$^{-1}$ (carbonyl group).

EXAMPLE 2

Preparation of 3-(1H-tetrazol-5-yl)Oxanilic Acid

Oxalyl chloride (12 g) was dissolved in 50 ml of anhydrous dimethoxyethane and a solution of 3-(1H-tetrazol-5-yl)aniline (5 g) in 250 ml of anhydrous dimethoxyethane was dropwise added to the solution obtained above over 3 hours at room temperature while stirring. Insolubles were removed by filtering the solution, then 50 ml of water was gradually added to the reaction mixture under ice cooling and stirring was continued for one hour at room temperature. Then, 500 ml of ethyl acetate was added thereto to carry out extraction, the extract was washed with water, dried over anhydrous sodium sulfate and then the solvent was distilled off to obtain 5.4 g of the objective product, 3-(1H-tetrazol-5-yl)oxanilic acid (yield 74.8%). The physical properties and spectral data of this product were consistent with those described in EXAMPLE 1.

EXAMPLE 3

Preparation of Potassium 3-(1H-tetrazol-5-yl)Oxanilate

Potassium hydroxide (1.27 g) was dissolved in 100 ml of ethanol and 5 g of 3-(1H-tetrazol-5-yl)oxanilic acid was added to the solution, followed by stirring at room temperature for 4 hours. Crystals separated out from the reaction solution were filtered off, washed with 50% aqueous solution of ethanol and dried under reduced pressure at 40° C. in the presence of phosphorous pentoxide to obtain 4.65 g of the objective potassium 3-(1H-tetrazol-5-yl)oxanilate (yield 85%). Decomposition point: not less than 300° C.

Elemental Analysis (for $C_9H_6N_5O_3K$)

|  | C (%) | H (%) | N (%) |
| --- | --- | --- | --- |
| Calcd. | 39.85 | 2.23 | 25.82 |
| Found | 39.06 | 2.50 | 24.61 |

I.R. Spectra (KBr disc): 1695 cm$^{-1}$ (carbonyl group).

According to the same procedures as those described above, sodium salt of the oxanilic acid was also prepared.

Elemental Analysis (for $C_9H_6N_5O_3Na$)

|  | C (%) | H (%) | N (%) |
| --- | --- | --- | --- |
| Calcd. | 42.32 | 2.35 | 27.43 |
| Found | 42.16 | 2.47 | 27.25 |

I.R. Spectra (KBr disc): 1685 cm$^{-1}$ (carbonyl group).

EXAMPLE 4

Preparation of Disodium 3-(1H-Tetrazol-5-yl)Oxanilate

Sodium hydroxide (1.72 g; 43 mmol) was dissolved in methanol (100 ml), 3-(1H-tetrazol-5-yl)oxanilic acid (5 g; 21.5 mmol) was added thereto and the mixture was stirred for 1 hour at room temperature. The reaction solution was poured into 300 ml of ethyl ether at room temperature with stirring, the precipitated crystals were filtered off and were dried at 40° C. in vacuo in the presence of phosphorous pentoxide to obtain 5 g (yield 85%) of disodium 3-(1H-tetrazol-5-yl)oxanilate. Decomposition point: not less than 300° C.

Elemental Analysis (for $C_9H_5N_5O_3Na_2$)

|  | C (%) | H (%) | N (%) |
| --- | --- | --- | --- |
| Calcd. | 39.01 | 1.81 | 25.26 |
| Found | 39.18 | 1.85 | 25.10 |

I.R. Spectra (KBr disc): 1680 cm$^{-1}$ (carbonyl group).

The histamine and SRS-A release inhibitory effect of the compound according to the present invention will hereunder be explained in more detail with reference to the following tests.

Test 1

Test on Effect for Inhibiting Release of Histamine and SRS-A from a Sectile of Lung Originated from a Sensitized Guinea Pig:

Anti-ovalbumin serum (0.5 ml/animal) was intravenously injected into a forepaw of a Hartley male guinea pig to cause passive sensitization.

After two days, the guinea pig was sacrificed by exsanguination and the lung was removed therefrom. The lung was cut into pieces of 1 mm square and then Tyrode's solution was added to the pieces of lung to form a suspension thereof. The suspension was treated for 5 minutes with a solution of a desired concentration obtained by dissolving the compound to be examined in 0.15 M phosphate buffer and then an antigen (ovalbumin) was added to the suspension, followed by the incubation for 15 minutes and then the supernatant was recovered to determine the amount of the histamine and SRS-A included therein. The measurement of the amount of histamine was effected according to the method of May C.D. et al. (Journal of Allergy, 1970, Vol. 46, pp. 12–20), while that of SRS-A was carried out according to the method of Watanabe et al. disclosed in Microbiology and Immunology, 1979, Vol. 23, pp. 1009–1022.

Results obtained are listed in the following Table I.

TABLE I

| Concn. of Drug* (g/ml) | Rate of Release Inhibitory (%) | | | | | |
| --- | --- | --- | --- | --- | --- | --- |
|  | MTCC His. | SRS-A | MTB His. | SRS-A | DSCG His. | SRS-A |
| $10^{-7}$ | 6 | 19 | 6 | 28 | — | — |
| $10^{-6}$ | 20 | 59 | 14 | 49 | — | — |
| $10^{-5}$ | 34 | 73 | 30 | 66 | — | 9 |

TABLE I-continued

| Concn. of Drug* (g/ml) | Rate of Release | | | Inhibitory (%) | | | |
|---|---|---|---|---|---|---|---|
| | MTCC | | MTB | | DSCG | | |
| | His. | SRS-A | His. | SRS-A | His. | SRS-A | |
| $10^{-4}$ | 21 | 65 | 37 | 64 | 2 | 13 | |

*The details of the drugs used are as follows:
MTCC (Compound of the Invention): 3-(1H—tetrazol-5-yl)oxanilic acid;
MTB: Butyl 3-(1H—tetrazol-5-yl)oxanilate;
DSCG: Disodium Chromoglycate Test 2

This test was carried out to examine the degranulation inhibitory effect of the compounds of the present invention on the metachromatic cells in nasal mucus originated from a rat suffering from experimental allergic rhinitis.

Method

Wistar rats were passively sensitized by subcutaneously injecting anti-Cryptomeria Japonica-Ascaris serum of rat. After anesthetizing the rat with pentobarbital sodium, they were fixed while lying them on their back and the cervixes thereof were subjected to median incision. A polyethylene tube having an outer diameter of 1 mm was inserted into the internal nares of each rat through the incised portion of trachea, one end thereof was connected to a perfusion pump and sterilized physiologic saline warmed at 37° C. was perfused therethrough at a flow rate of 0.25 ml/min. 1 ml of the antigen extracted from pollen of Japanese cedar (10 micro liter per ml) was sprayed in both internal nares by means of an atomizer for internal nares and the perfusate delivered from the internal nares was recovered for 20 minutes. The number of degranulated cells per 100 metachromatic cells present in the recovered samples were scored and the value was regarded as that of the control (Nc).

The compound to be tested were dissolved in 0.15M phosphate buffer so as to obtain a solution of a desired concentration, each solution was administered through both of the interanal nares in an amount of 0.5 ml/100 g body weight, at a time 5 minutes before the spray of the antigen and the number of degranulated cells (Nt) was scored according to the same manner as described above. The rate of inhibitory effect on the degranulation (Rd) was estimated from the following relation:

$$Rd\ (\%) = \frac{Nc - Nt}{Nc} \times 100$$

Results obtained are shown in Table II below. Each experimental results is the average of 5 measurements.

TABLE II

| Concn. (g/ml) | Rate of Inhibition of Degranulation Rd (%) | |
|---|---|---|
| | MTCC | DSCG |
| $10^{-8}$ | −1.4 | −1.7 |
| $10^{-7}$ | 15.0 | 8.1 |
| $10^{-6}$ | 33.0 | 39.4 |
| $10^{-5}$ | 75.1 | 71.5 |
| $10^{-4}$ | 94.3 | 90.3 |

Test 3

This test was effected to examine the nasal mucus secretion inhibitory effect of the compounds according to the present invention on the rats suffering from experimental allergic rhinitis.

Method

Wistar rats were passively sensitized by subcutaneously injecting anti-Cryptomeria Japonica-As serum of rat. After anesthetizing the rat with pentobarbital sodium, they were fixed while lying them on their back and the cervixes thereof were subjected to median incision. A polyethylene tube having an outer diameter of 1 mm was inserted into the internal nares of each rat through the incised portion of trachea, one end thereof was connected to a perfusion pump and sterilized physiologic saline warmed at 37° C. was perfused therethrough at a flow rate of 0.25 ml/min.

Then, 0.5 ml/100 g body weight of 4% brilliant blue was injected into the rat through the caudal vein, then the perfusate was recovered for 10 minutes and the concentration of the dye was determined which was regarded as the Ag (−) value of the control. 1 ml of the antigen extracted from pollen of Japanese cedar (1 micro liter per ml) was sprayed in both internal nares by means of an atomizer for internal nares, the antigen remaining in the internal nares was washed out with physiologic saline and the perfusate was then recovered for 30 minutes and the concentration of the dye was determined to estimate Ag (+) value of the control.

The compound to be tested were dissolved in 0.15 M phosphate buffer so as to form a solution of a desired concentration. Each of the solutions thus prepared was sprayed in both internal nares in an amount of 0.5 ml/100g body weight at the time of 5 minutes before the spray of the antigen and the concentration of the dye was determined on each sample. In this connection, the measurement of the dye concentration was effected according to the spectrophotometric method developed by M. Kojima et al. (Allergy, 1986, Vol. 35, pp. 180–187).

Results

Results observed in this test are listed in the following Table III. Each experimental result is the average of 5 measurements.

TABLE III

| Concn. (g/ml) | Dye Concentration (micro gr./ml) | |
|---|---|---|
| | MTCC | DSCG |
| $10^{-8}$ | 1.74 | 1.77 |
| $10^{-7}$ | 1.37 | 1.44 |
| $10^{-6}$ | 0.99 | 1.01 |
| $10^{-5}$ | 0.85 | 0.89 |
| $10^{-4}$ | 0.64 | 0.65 |

Test 4

This test was carried out to estimate the therapeutic effect of the compounds according to the present invention on the allergic conjunctivitis of guinea pigs.

Hartley guinea pigs were passively sensitized by intravenously injecting 1 ml of anti-DNP-As serum. After 8 days, an antigen solution (DNP-BSA: 2.5 mg/ml) was dropped on the sinistral eye once a minute over 10 minutes, then the lacrimal fluid was collected with filter paper over 10 minutes while the inflammatory reaction of the eye was visually observed during the collection of the lacrimal fluid. At 10 minutes after the completion of the dropping of the antigen solution, the compounds to be examined were dropped on the eye once a minute over 10 minutes and thereafter the collection of the lacrimal fluid and the visual observation of the inflammatory reaction of the eye were likewise effected. Then, the amount of histamine present in the collected lacrimal fluid was determined according to the Komatsu's method (Michitoshi KOMATSU, Allergy, 1978, Vol. 27, pp. 67-74).

In addition, the concentration of MTCC used was $10^{-3}$ g/ml and that of DSCG was $2\times10^{-2}$ g/ml.

Results (1) Visual Observation of the Inflammatory Reaction

The severe swelling, congestion and dacryorrhea of the conjunctiva were observed on all of the animals tested by the dropping of the antigen solution on the eye. Among these reactions, an excellent therapeutic effect was observed so far as the swelling and congestion of the conjuctiva were concerned, due to the subsequent dropping of the MTCC solution. Moreover, it was evidenced that the comparative sample (DSCG) presents a relatively low therapeutic effect to these symptom compared with MTCC.

(2) Measurement of the Histamine Content

Results are summarized in the following Table IV.

TABLE IV

| (ng) | Histamine Content in Lacrimal Fluid | |
| --- | --- | --- |
| | MTCC | DSCG |
| After Dropping of Antigen | 6.3 | 6.7 |
| After Dropping of Compound | 2.4 | 6.4 |

As seen from the results listed in Table IV, the histamine content in the lacrimal fluid was substantially reduced by the administration of MTCC. Furthermore, the reduction in the histamine content approximately coincides with the results on the therapeutic effect estimated by visual observation of the inflammation of the eye.

Test 5

Acute Toxicity Test of MTCC

MTCC was administered to ddY Mice (body weight 20 to 23 g; 10 animals per test group) and Wistar rats (body weight 110 to 130 g; 10 animals per test group) through intravenous and oral routes and it was also administered to Beagle dogs (7 months old; 3 animals per test group) through oral route. The symptom of these test animals was observed for 14 days after the administration of MTCC and $LD_{50}$ was estimated from the number of animals died during this term.

MTCC was administered to rats and mice in the form of a solution thereof in 0.1 M phosphate buffer in the case of intravenous administration and in the form of a suspension in 0.5% CMC-Na in the case of oral administration. While it was orally administered to dogs in the form of a capsule filled with the original powder.

The acute toxicity of MTCC with respect to rats, mice and dogs thus obtained are shown in Table V.

TABLE V

| | Acute Toxicity $LD_{50}$ (mg/kg) | |
| --- | --- | --- |
| | Administration Route | |
| Test Animal | i.v. | p.o. |
| Mouse Male | >225 | >2000 |
| Female | >225 | >2000 |
| Rat Male | >180 | >2000 |
| Female | >180 | >2000 |
| Dog Male | — | >2000 |
| Female | — | >2000 |

The compound according to the present invention is preferably used in the form of an aqueous solution or an inhalant capable of administering even to the deep portion of the bronchus as fine particles of such a solution. However, in the present invention, it is not intended to limit the pharmaceutical preparations to this particular form and other dosage forms such as injectable solutions, resolvents for eye drop and nasal drop, as well as other forms such as solid medicines, for instance, powdered drugs, injectable powder, tablets, capsules, or the like suitable for administering through various routes are also possible. Therefore, a variety of pharmaceutically acceptable additives such as stabilizers, excipients, diluents, isotonicities, carriers and the like which are well known in the art may be added to the pharmaceutical preparations containing the compound of the present invention.

The compounds according to the present invention presents an excellent histamine and SRS-A release inhibitory effect as described above and, therefore, they can effectively be employed to prepare, in particular, aqueous preparations thereof (antiallergic agent) for use in treating or preventing allergic diseases, such as bronchial asthma, rhinitis and conjunctivitis. In such case, the sodium salt or potassium salt is preferably used to form such pharmaceutical preparations, although the acid per se can of course be utilized. Some pharmaceutical preparations containing the compounds according to the present invention will hereunder be explained for the purpose of illustration.

EXAMPLE OF PREPARATION 1

Inhalant

Anhydrous sodium phosphate (80 g) was dissolved in about 500 ml of pure water and 20 g of the compound according to the present invention was dissolved in the solution. Then, the resultant solution was adjusted to pH 7.4 with the addition of aqueous sodium hydroxide solution, sodium chloride and mannitol as the isotonicity were added and then water was added so as to correctly form 1 liter of the intended solution. Thereafter, the resultant solution was filtered according to a conventional manner and dispensed into vials and thus inhalant having a concentration of 2% was prepared. This preparation is suitable for treating and preventing bronchial asthma and is administered through inhalation route using a nebulizer.

EXAMPLE OF PREPARATION 2

Injectable Liquid, Resolvent for Eye Drop or Nasal Drop

An injectable liquid, a resolvent for eye drop or nasal drop having a concentration of 1% was prepared according to the same procedures as those described in EXAMPLE OF PREPARATION 1 except that 10 g of the compound according to the present invention was used. The nasal drop thus obtained is locally administered using a quantitative atomizer.

EXAMPLE OF PREPARATION 3

Powdery Inhalant

A mixture was prepared by uniformly admixing 400 g of the compound of the present invention having a particle size of not more than 10 microns and 600 g of lactose having a particle size of 30 to 60 microns. The mixture was then divided into portions of 50 mg each which was charged into No. 2 capsules to obtain objective powdery inhalant. This preparation is suitable for treating and preventing bronchial asthma and is administered using a powder inhaler.

What is claimed is:

1. 3-(1H-tetrazol-5-yl)oxanilic acid and pharmaceutically acceptable salt thereof.

2. The compound as set forth in claim 1 in which the compound is in the form of the sodium, disodium or potassium salt thereof.

3. A pharmaceutical composition for treating or preventing allergic diseases comprising 3-(1H-tetrazol-5-yl)oxanilic acid or a pharmaceutically acceptable salt thereof as an effective component.

4. The pharmaceutical composition for treating or preventing allergic diseases as set forth in claim 3 in which the effective component is the sodium, disodium or potassium salt of 3-(1H-tetrazol-5-yl)oxanilic acid.

5. The pharmaceutical composition for treating or preventing allergic diseases as set forth in claim 3 in which the pharmaceutical composition is in the form of an inhalant, a resolvent for eye drop or nasal drop.

6. The pharmaceutical composition for treating or preventing allergic diseases as set forth in claim 3 wherein the pharmaceutical composition is in the form of an aqueous solution.

* * * * *